(12) United States Patent
Malamas

(10) Patent No.: US 7,141,672 B2
(45) Date of Patent: *Nov. 28, 2006

(54) OXAZOLE-ARYL-CARBOXYLIC ACIDS USEFUL IN THE TREATMENT OF INSULIN RESISTANCE AND HYPERGLYCEMIA

(75) Inventor: Michael S. Malamas, Jamison, PA (US)

(73) Assignee: Wyeth, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/753,792

(22) Filed: Jan. 8, 2004

(65) Prior Publication Data

US 2004/0147755 A1 Jul. 29, 2004

Related U.S. Application Data

(62) Division of application No. 09/307,923, filed on May 10, 1999, now Pat. No. 6,699,896.

(60) Provisional application No. 60/113,661, filed on May 12, 1998.

(51) Int. Cl.
| | |
|---|---|
| C07F 9/00 | (2006.01) |
| C07D 417/00 | (2006.01) |
| C07D 285/00 | (2006.01) |
| C07D 271/00 | (2006.01) |
| C07D 277/00 | (2006.01) |

(52) U.S. Cl. .............. 546/268.7; 546/22; 546/269.1; 546/269.7; 546/270.4; 548/112; 548/130; 548/132; 548/181; 548/183; 548/202; 548/203; 548/204; 548/205

(58) Field of Classification Search ............ 546/22, 546/268.7, 269.1, 269.7, 270.4; 548/112, 548/130, 132, 181, 183, 202, 203, 204, 205
See application file for complete search history.

(56) References Cited

U.S. PATENT DOCUMENTS

| | | | | |
|---|---|---|---|---|
| 3,666,473 | A | 5/1972 | Colom et al. ............ 96/91 D |
| 4,117,151 | A | 9/1978 | Deschamps et al. ...... 424/285 |
| 4,153,703 | A * | 5/1979 | Harrison et al. ........... 514/365 |
| 4,808,599 | A | 2/1989 | Dubroeucq et al. ........ 514/320 |
| 5,235,064 | A | 8/1993 | Gapinski ................... 548/253 |
| 5,334,598 | A | 8/1994 | Bagley et al. .............. 514/303 |
| 5,523,302 | A | 6/1996 | Cain et al. ................. 514/252 |
| 5,596,106 | A | 1/1997 | Cullinan et al. ............. 549/57 |
| 5,688,821 | A | 11/1997 | Kees ......................... 514/371 |
| 5,698,574 | A | 12/1997 | Riedl et al. ................. 514/376 |
| 6,232,322 | B1 | 5/2001 | Malamas ................... 514/303 |
| 6,391,897 | B1 | 5/2002 | Malamas ................... 514/340 |
| 6,699,896 | B1 * | 3/2004 | Malamas ................... 514/374 |

FOREIGN PATENT DOCUMENTS

| | | |
|---|---|---|
| DE | 1249869 | 9/1967 |
| DE | 1291197 | 3/1969 |
| DE | 2616414 | 10/1977 |
| DE | 3110460 | 12/1982 |
| DE | 3342624 | 3/1984 |
| EP | 0092239 | 10/1983 |
| EP | 0276064 | 7/1988 |
| EP | 0382199 | 8/1990 |
| EP | 0568289 | 11/1993 |
| EP | 0629624 | 12/1994 |
| EP | 0693491 | 1/1996 |
| GB | 1293396 | 11/1969 |
| JP | 58150948 | 9/1983 |
| JP | 60172946 | 9/1985 |
| JP | 6236661 | 2/1987 |
| JP | 6236662 | 2/1987 |
| JP | 63161449 | 7/1988 |
| JP | 3247655 | 11/1991 |
| JP | 4016854 | 1/1992 |
| JP | 6348018 | 12/1994 |
| WO | 9111909 | 8/1991 |
| WO | 9422834 | 10/1994 |
| WO | 9422835 | 10/1994 |
| WO | 9608483 | 3/1996 |
| WO | 9609818 | 4/1996 |
| WO | 9634851 | 11/1996 |
| WO | 9721693 | 6/1997 |

OTHER PUBLICATIONS

Ahmad, F. et al., Biochemica et Biophysica Acta, 1248, 1995, pp. 57-69.
Chang, A. Y. et al., Diabetes, 32, 1983, pp. 830-838.
Coleman, D. L., Diabetologia, 14, 1978, pp. 141-148.
DeFronzo, R. A. et al., Diabetes Care, 14:3, 1991, pp. 173-194.
Goldstein, B. J., Receptor, 3, 1993, pp. 1-15.
Goldstein, B. J. et al., Mol. and Cell. Biochem., 109, 1992, pp. 107-113.

(Continued)

Primary Examiner—Brenda Coleman
(74) Attorney, Agent, or Firm—Fish & Richardson P.C.

(57) ABSTRACT

This invention provides compounds of Formula I having the structure

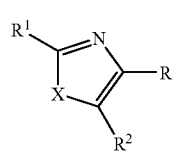

or a pharmaceutically acceptable salt thereof, which are useful in treating metabolic disorders related to insulin resistance or hyperglycemia.

7 Claims, No Drawings

OTHER PUBLICATIONS

Goldstein, B. J., J. Cell. Biochem., 48, 1992, pp. 33-42.
Haring, H. U., Diabetologia, 34, 1991, pp. 848-861.
Harris, M. I. et al., Diabetes in America, 1985, Chapter 29, pp. 1-48.
Jarrett, R. J., Diabetes/Metabolism Reviews, 5:7, 1989, pp. 547-558.
Lanzetta, P. A. et al., Analytical Biochem. 100, 1979, pp. 95-97.
McGuire, M. C. et al., Diabetes, 40, Jul. 1991, pp. 939-942.
Meyerovitch, J. et al., J. Clin. Invest., 87, Apr. 1991, pp. 1286-1294.
Meyerovitch, J. et al., J. Clin. Invest., 84, Sep. 1989, pp. 976-983.
Mitsunobu, O., Synthesis, Jan. 1981, pp. 1-28.
Nutaitis, C. F., Organic Preparations and Procedures Int., 23(4), 1991, pp.403- 411.
Perich, J. W. et al., Synthesis, Feb. 1988, pp. 142-144.
Phillion, D. P. et al., Tetrahedron, 27:13, 1986, pp. 1477-1480.
Pyorala, K. et al., Diabetes/Metabolism Reviews, 3:2, 1987, pp. 463-524.
Reaven, G. M. et al., Amer. J. Med., 60, 1976, pp. 80-88.
Sredy, J. et al., Metabolism, 44:8, 1995, pp. 1074-1081.
Stout, R. W. Metabolism, 34:12 (Suppl 1), Dec. 1985, pp. 7-12.
Zask, A. et al., J. Med. Chem., 33, 1990, pp. 1418-1423.
Chen, H.-M. et al., Indian J. Chem., 35B, Dec. 1996, pp. 1304-1307.
d'Ischia, M. et al., Tetrahedron, 43:2, 1987, pp. 431-434.
Dryhurst, G. et al., J. Am. Chem. Soc., 111, 1989, pp. 719-726.
Guirguis, N. R. et al., J. Parkt. Chemie, 332:3, 1990, pp. 414-418.
Guirguis, N. R. et al., Liebigs Ann. Chem., 1986, pp. 1003-1011.
Hashem, A. I., J. Prakt. Chemie, 319:4, 1977, pp. 689-692.
Konopelski, J.P. et al., Synlett, Letters, Jul. 1996, pp. 609-611.
Kuroda, T. et al., J. Org. Chem., 59, 1994, pp. 7353-7357.
Kuroda, T. et al., J. Chem. Soc., Chem. Commun., 1991, pp. 1635-1636.
Lefker, B. A. et al., Tetrahedron Letters, 35:29, 1994, pp. 5205-5208.
Molina, P. et al., Tetrahedron, 50:17, 1994, pp. 5027-5036.
Molina, P. et al., Tetrahedron Letters, 34:17, 1993, pp. 2809-2812.
Napolitano, A. et al., Tetrahedron, 45:21, 1989, pp. 6749-6760.
Schuster, I. I., et al., J. Org. Chem., 53, 1988, pp. 5819-5825.
Buu-Hoi, N. P. et al., J. Chem. Soc., 1957, pp. 625-628.
Brown, E. V. et al., J. Med. Chem., 14:1, 1971, pp. 84-85.
Kimura, T. et al., Tetrahedron Letters, 36:7, 1995, pp. 1079-1080.
Han, B. H. et al., Tetrahedron Letters, 31:8, 1990, pp. 1181-1182.
Kano, S. et al., Heterocycles, 19:6, 1982, pp. 1033-1037.
Martin, S.F. et al., J. Org. Chem., 49, 1984, pp. 2512-2513.
Eckert, T. et al., Arch. Pharm., 315, 1982, pp. 569-570.
Goldenberg, C. et al., Eur. J. Med. Chem., Chim. Ther., 12:1, Jan.-Feb. 1977, 81-86.
Artini, D. et al., Arzneim.-Forsch. (Drug Res.), 21:1, 1971, pp. 30-36.
Ayyangar, N.R. et al., Synthesis, Apr. 1991, pp. 322-324.
Darchen, A. et al., J.C.S. Chem. Comm., 1976, p. 820.
De Cointet, P. et al., Chimie Therapeutique, 5, Sep.-Oct. 1973, pp. 574-587.
Hamacher, H., Arch. Pharmaz., 308/75, pp. 290-301, 1975.
Massolini, G. et al., Il Farmaco, 45(2), 1990, pp. 263-268.
Miyaura, N. et al., Synthetic Communications, 11:7, 1981, pp. 513-519.
Barraclough, P. et al., Arch. Pharm., 323, 1990, pp. 507-512.
Liebeskind, L. S. et al., J. Org. Chem., 55, 1990, pp. 5359-5364.
Toth, I., Liebigs Ann. Chem., 1994, pp. 685-688.
Katritsky, A.R. and Weeds, S.N., "The literature of heterocyclic chemistry", *Advances in Heterocyclic Chemistry*, 7, 225, Academic Press, New York (1966).
Katritsky, A.R., "The literature of heterocyclic chemistry", *Advances in Heterocyclic Chemistry*, 55, 31, Academic Press, New York (1992).
Miyaura et al., "Palladium-Catalyzed Cross-Coupling Reactions of Organoboron Compounds", *Chem. Rev.*, 95:2457-2483 (1995).
Miyaura et al., "The Palladium-Catalyzed Cross-Coupling Reaction of Phenylboronic Acid with Haloarenes in the Presence of Bases", *Synthetic Communications*, 11(7):513-519 (1981).
Thompson et al., "A General Synthesis of 5-Arylnicotinates", *J. Org. Chem.*, 49:5237-5243 (1984).

* cited by examiner

OXAZOLE-ARYL-CARBOXYLIC ACIDS USEFUL IN THE TREATMENT OF INSULIN RESISTANCE AND HYPERGLYCEMIA

This application is a divisional of U.S. application Ser. No. 09/307,923, filed on May 10, 1999 (Now U.S. Pat. No. 6,699,896), which claims the benefit of U.S. Provisional Application No. 60/113,661, which was converted from U.S. patent application Ser. No. 09/076,710, filed May 12, 1998, pursuant to a petition filed under 37 C.F.R. 1.53(c)(2)(i) on Jul. 6, 1998.

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia with obesity and with ischemic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989,5, 547; Harris et al, Mortality from diabetes, in *Diabetes in America* 1985).

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPα and SH-PTP2 (B. J. Goldstein, *J. Cellular Biochemistry* 1992, 48, 33; B. J. Goldstein, *Receptor* 1993, 3, 1–15,; F. Ahmad and B. J. Goldstein *Biochim. Biophys Acta* 1995, 1248, 57–69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion failed to suppress PTPase activity as it did in insulin sensitive subjects.

Meyerovitch et al (*J. Clinical Invest.* 1989, 84, 976) observed significantly increased PTPase activity in the livers of two rodent models of IDDM, the genetically diabetic BB rat, and the STZ-induced diabetic rat. Sredy et al (*Metabolism,* 44, 1074, 1995) observed similar increased PTPase activity in the livers of obese, diabetic ob/ob mice, a genetic rodent model of NIDDM.

The compounds of this invention have been shown to inhibit PTPases derived from rat liver microsomes and human-derived recombinant PTPase-1B (hPTP-1B) in vitro. They are useful in the treatment of insulin resistance associated with obesity, glucose intolerance, diabetes mellitus, hypertension and ischemic diseases of the large and small blood vessels.

DESCRIPTION OF THE INVENTION

This invention provides a compound of formula I having the structure

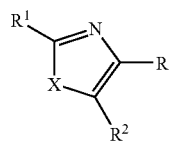

wherein

R is 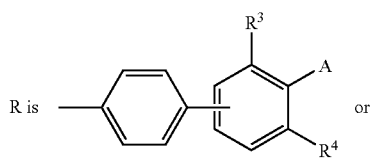 or

-continued

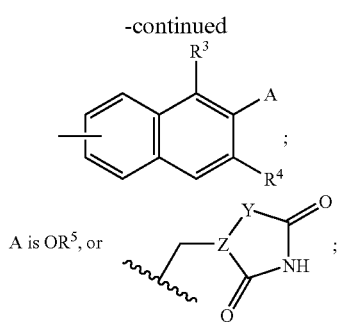

A is $OR^5$, or

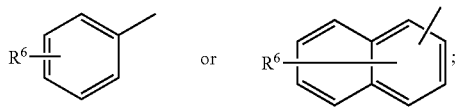

$R^1$ is alkyl of 1–6 carbon atoms, cycloalkyl of 3–8 carbon atoms, thienyl, furyl, pyridyl,

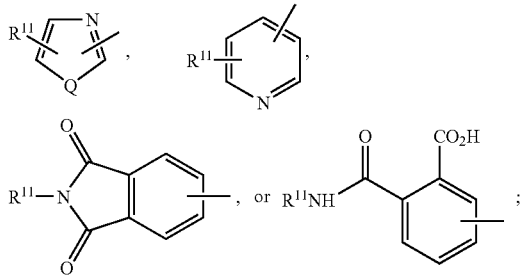

$R^2$ is hydrogen, alkyl of 1–6 carbon atoms, or aryl of 6 to 10 carbon atoms;

$R^3$ and $R^4$ are independently halogen, hydrogen, alkyl of 1–12 carbon atoms, aryl of 6 to 10 carbon atoms; halogen, trifluoromethyl of 1–6 carbon atoms, alkoxyaryl of 7–14 carbon atoms; nitro, amino, carboalkoxy, carbamide, carbamate, urea, alkylsulfoamide, —$NR^7(CH_2)_mCO_2H$, arylsulfoamide, cycloalkyl of 3–8 carbon atoms, or heterocycle of 5 to 7 atom rings containing from 1 to 3 heteroatoms selected from oxygen, nitrogen, or sulfur;

$R^5$ is hydrogen, alkyl of 1–6 carbon atoms, —$CH(R^8)R^9$, —$C(CH_2)_nCO_2R^{10}$, —$C(CH_3)_2CO_2R^{10}$, —$CH(R^8)(CH_2)_nCO_2R^{10}$, —$CH(R^8)C_6H_4CO_2R^{10}$, or —$CH_2$-tetrazole;

$R^6$ is hydrogen, alkyl of 1–6 carbon atoms, halogen, alkyoxy of 1–6 carbon atoms, trifluoroalkyl of 1–6 carbon atoms or trifluoroalkoxy of 1–6 carbon atoms;

$R^7$ is hydrogen or alkyl of 1 to 6 carbon atoms;

$R^8$ is hydrogen, alkyl of 1–6 carbon atoms, aryl of 6–10 carbon atoms, arylalkyl of 7–15 carbon atoms, cycloalkyl of 3–8 carbon atoms, phthalic acid, $R^9$ is $CO_2R^{12}$, $CONHR^{12}$, tetrazole, $PO_3R^{12}$;

$R^{10}$ is hydrogen, alkyl of 1–6 carbon atoms, aryl of 6–12 carbon atoms, aralkyl of 7–15 carbon atoms;

$R^{11}$ is alkylene of 1 to 3 carbon atoms;

$R^{12}$ is hydrogen, alkyl of 1–6 carbon atoms, aryl of 6–12 carbon atoms, aralkyl of 7–15 carbon atoms;

X is O, or S;
Y is O, N, or S;
Z is C, or N;
Q is O, N, or S;
m=1–3;
n=1–6, or a pharmaceutically acceptable salt thereof, which are useful in treating metabolic disorders related to insulin resistance or hyperglycemia.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Alkyl includes both straight chain as well as branched moieties. Halogen means bromine, chlorine, fluorine, and iodine. It is preferred that the aryl portion of the aryl or aralkyl substituent is a phenyl, naphthyl or 1,4-benzodioxan-5-yl group; with phenyl being most preferred. The aryl moiety may be optionally mono-, di-, or tri-substituted with a substituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —$CO_2H$, alkylcarbonyloxy of 2–7 carbon atoms, and alkylcarbonyl of 2–7 carbon atoms.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable-salts thereof.

Preferred compounds of this invention are those compounds of Formula I, X is oxygen. More preferred compounds of this invention are those compounds of Formula I, wherein:

X is O;
$R^1$ is phenyl substituted with $R^6$;
$R^2$ is alkyl of 1–6 carbon atoms; and
$R^3$ and $R^4$ are each, independently, hydrogen or halogen.

Specifically preferred compounds of the present invention are set forth below:

4-(4'-methoxy-biphenyl-4-yl)-5-methyl-2-(4-trifluoromethyl-phenyl)-oxazole 4-(4'-methoxy-biphenyl-3-yl)-5-methyl-2-(4-trifluoromethyl-phenyl)-oxazole 4'-[5-methyl-2-(4-trifluoromethyl-phenyl)-oxazol-4-yl]-biphenyl-4-ol 3'-[5-methyl-2-(4-trifluoromethyl-phenyl)-oxazol-4-yl]-biphenyl-4-ol {4'-[5-methyl-2-(4-trifluoromethyl-phenyl)-oxazol-4-yl]-biphenyl-4-yloxy}-acetic acid {3'-[5-methyl-2-(4-trifluoromethyl-phenyl)-oxazol-4-yl]-biphenyl-4-yloxy}-acetic acid 2-{4'-[5-methyl-2-(4-trifluoromethyl-phenyl)-oxazol-4-yl]-biphenyl-4 yloxy}-3-phenyl-propionic acid 2-{3'-[5-methyl-2-(4-trifluoromethyl-phenyl)-oxazol-4-yl]-biphenyl-4-yloxy}-3-phenyl-propionic acid 3,5-dibromo-4'-[5-methyl-2-(4-trifluoromethyl-phenyl)-oxazol-4-yl]-biphenyl-4-ol
{3,5-dibromo-4'-[5-methyl-2-(4-trifluoromethyl-phenyl)-oxazol-4-yl]-biphenyl-4-yloxy}-acetic acid
2-{3,5-dibromo-4'-[5-methyl-2-(4-trifluoromethyl-phenyl)-oxazol-4-yl]-biphenyl-4-yloxy}-3-phenyl-propionic acid methyl ester
2-{3,5-dibromo-4'-[5-methyl-2-(4-trifluoromethyl-phenyl)-oxazol-4-yl]-biphenyl-4-yloxy}-3-phenyl-propionic acid
2-{4'-[5-methyl-2-(4-trifluoromethyl-phenyl)-oxazol-4-yl]-biphenyl-4-ylmethyl}-[1,2,4]oxadiazolidine-3,5-dione
2-{4'-[5-methyl-2-(4-trifluoromethyl-phenyl)-oxazol-4-yl]-biphenyl-3-ylmethyl}-[1,2,4]oxadiazolidine-3,5-dione
5-{4'-[5-methyl-2-(4-trifluoromethyl-phenyl)-oxazol-4-yl]-biphenyl-4-yloxymethyl}-1H-tetrazole or a pharmaceutically acceptable salt thereof.

The compounds of this invention were be prepared according to the following schemes from commercially available starting materials or starting materials which can be prepared using to literature procedures. These Schemes show the preparation of representative compounds of this invention.

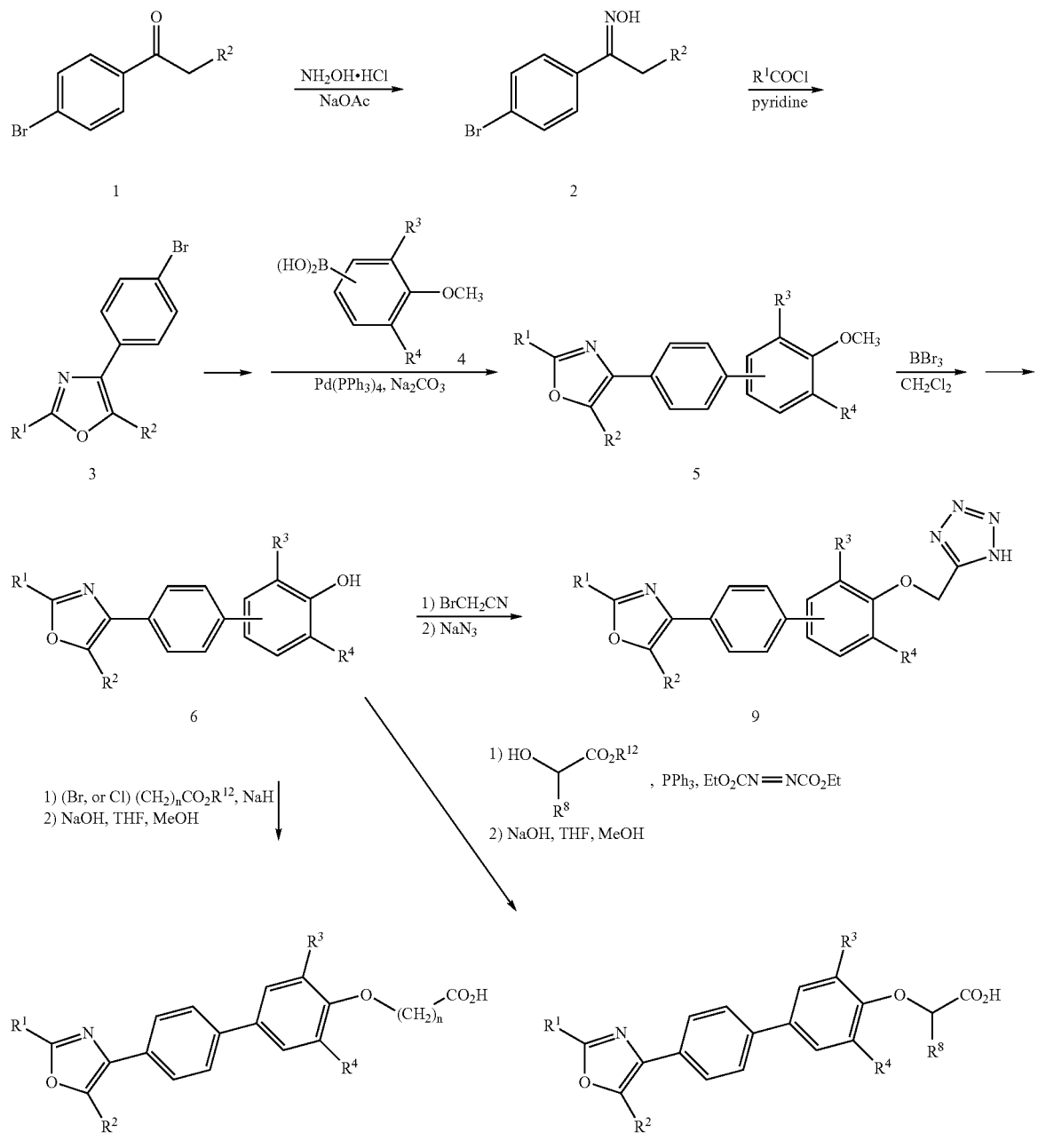

Scheme I

In Scheme I commercially available ketones (1) were treated with hydroxylamine in the presence of sodium acetate to produce oximes (2). Oximes (2) were converted to oxazoles by a known methodology [ref. Tet. Lett. 1980, 21, 2359–2360], where oximes (2) were treated with acetyl chlorides in the presence of pyridine to produce oxazoles (3). Oxazoles (3) were coupled with aryl boronic acids of general structure (4; $R^3$, $R^4$ are alkyl, aryl, trifluoromethyl, substituted aryl, nitro, carbocyclic 5 to 7 carbon atoms rings or heterocyclic rings 5 to 7 atom rings with from 1 to 3 heteroatoms selected from oxygen, nitrogen, and sulfur) using the Suzuki protocol [ref. Syn. Comm. 1981, 11, 513–519] to produce biphenyls (5). The aryl boronic acids are either commercially available or can be prepared according to known methodology [ref. J. Org. Chem, 1984, 49, 5237–5243]. Biphenyls (5) converted to phenols (6) by treatment with boron tribromide in dichloromethane [ref. J. Org. Chem. 1974, 39, 1427–1429]. Phenols (6) were alkylated with bromo or chloro-alkylcarboxylates [(Br or Cl)$(CH_2)_nCO_2R^{12}$] in the presence of sodium hydride or potassium carbonate, using dimethylformamide or acetonitrile as the solvent. Subsequent saponification with sodium hydroxide in methyl alcohol and tetrahydrofuran produced biphenyls (7). Coupling of biphenyls (6) with hydroxy-alkylcarboxylates [$HOCH(R^8)CO_2R^{12}$] using the Mitsunobu protocol [ref. *Synthesis.* 1981, 1–27], followed by saponification with sodium hydroxide in methyl alcohol and tetrahydrofuran produced biphenyls (8). Tetrazoles (9) were prepared from phenols (6) in a two step sequence. First the phenols (6) were alkylated with bromoacetonitrile in the presence of sodium hydride, and secondly, the nitrile was converted to tetrazoles (9) with sodium azide.

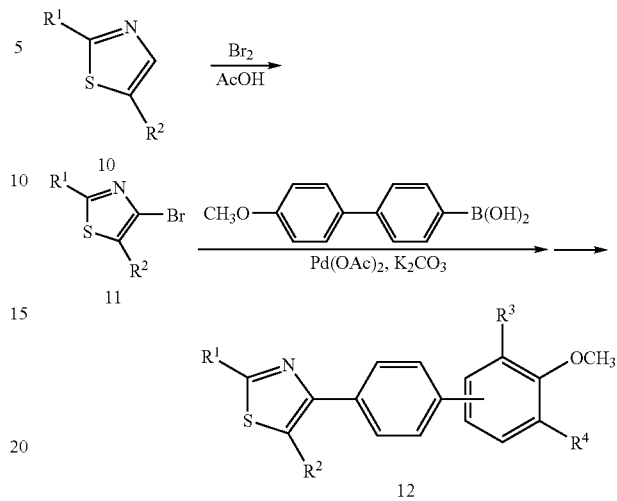

In Scheme II thiazoles (10) were brominated with bromine in the presence of sodium acetate. The 4-bromothiazoles (11) were coupled with 4,4'-methoxy biphenyl boronic acid using the Suzuki protocol [ref. Syn. Comm. 1981, 11, 513–519] to give biphenyls (12). Biphenyls (12) were further converted to the desired products in substantially the same manner as described in Scheme I.

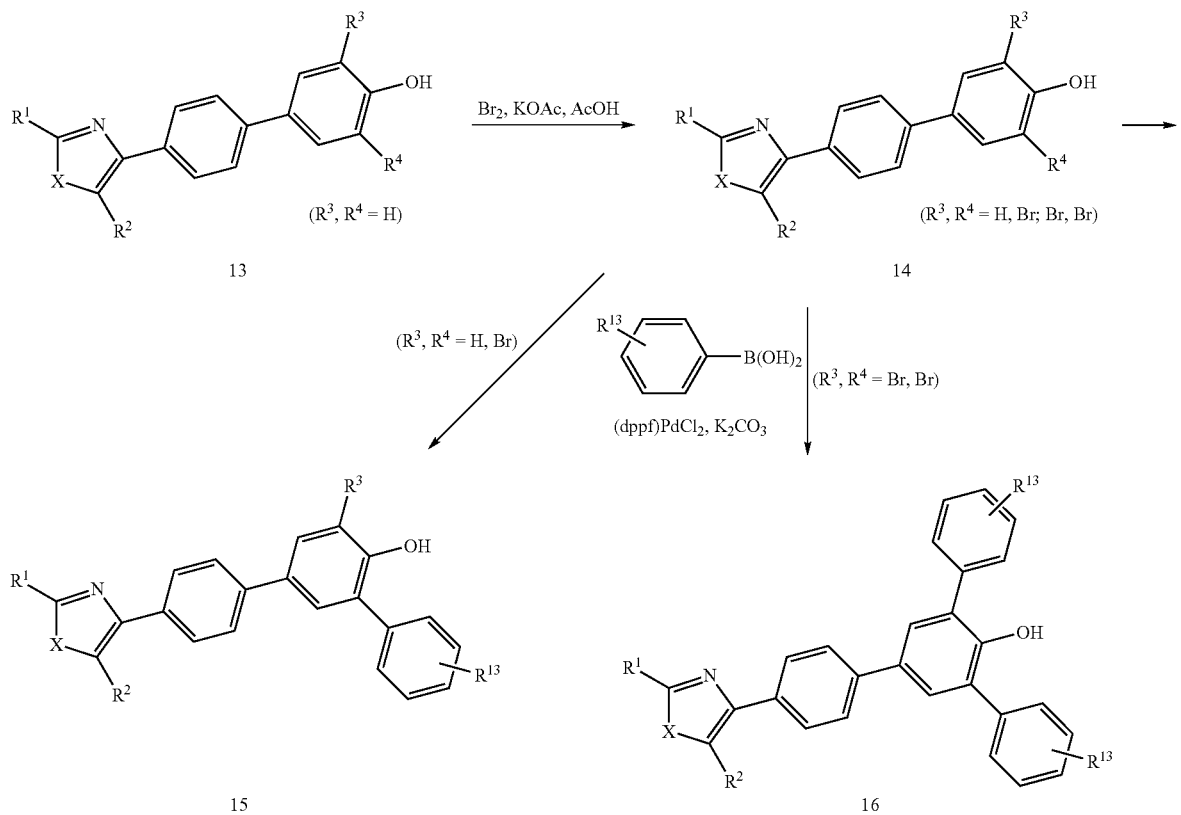

In Scheme III, the biphenyl compounds (13) can be monobrominated or dibrominated using bromine, potassium acetate and acetic acid. One equivalent of bromine in a high dilution reaction mixture and low temperatures in the range of 5–10° C. afforded predominantly the monobrominated product (14; $R^3$, $R^4$=H, Br). The dibrominated product (14; $R^3$, $R^4$=Br, Br) was obtained with two equivalents of bromine at room temperature. The Suzuki coupling protocol [ref. Syn. Comm. 1981, 11, 513–519] was used to generate the terphenyls 15 and 16. Coupling of the monobromo compounds (14; $R^3$, $R^4$=H, Br) with boronic acids $R^{13}$—Ar—B(OH)$_2$; ($R^{13}$=halogen, trifluoromethyl, alkoxy, alkyl, nitro, amino, carboalkoxy) in the present of an inorganic base, for example $K_2CO_3$, or $Ba(OH)_2$, and palladium (0 or II) catalyst, for example Pd(PPh3)$_4$, Pd(OAc)$_2$, or (dppf)PdCl$_2$, produced terphenyls (15; $R^3$=H). Similarly, the dibromo compounds (14; $R^3$, $R^4$=Br, Br) can undergo Suzuki coupling to afford either the di-coupled product (16) by using 2 equivalents of boronic acid at high temperatures (100° C.), or the mono-coupled-mono-bromo product (15; $R^3$, $R^4$=Br, Aryl-$R^{13}$). Both the bromo and dibromo compounds can afford in the same synthetic manner products with various heterocyclic boronic acids, for example thiophene, furan, oxazole, thiazole, pyridine.

Scheme IV

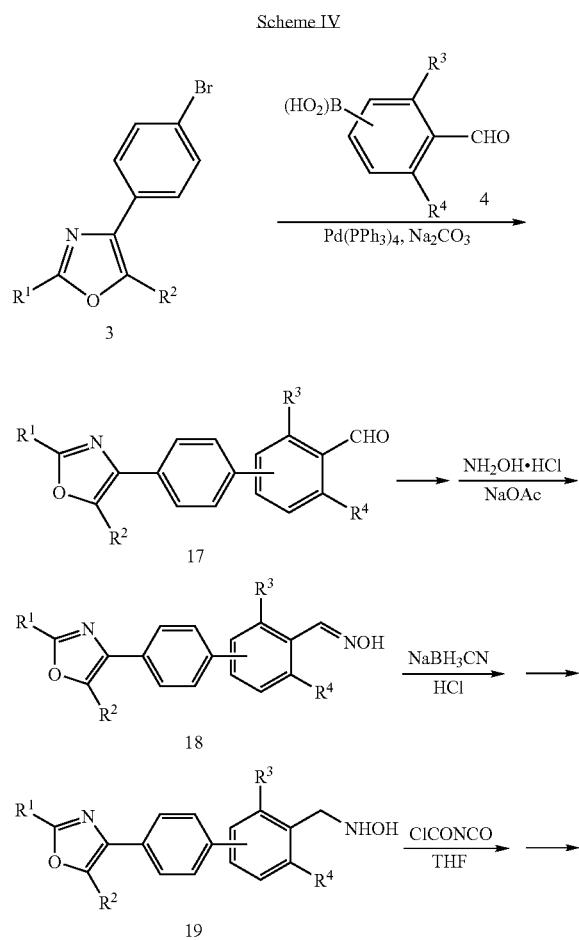

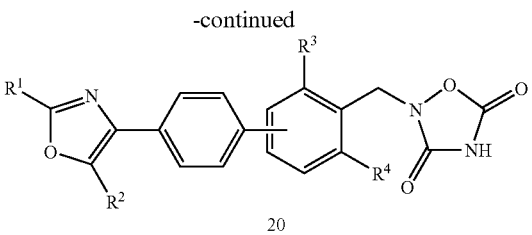

In Scheme IV oxazoles (3) were coupled with aryl boronic acids of general structure (4; $R^3$, $R^4$ are alkyl, aryl, trifluoromethyl, substituted aryl, nitro, carbocyclic 5 to 7 carbon atoms rings or heterocyclic rings 5 to 7 atom rings with from 1 to 3 heteroatoms selected from oxygen, nitrogen, and sulfur) using the Suzuki protocol [ref. Syn. Comm. 1981, 11, 513–519] to produce biphenyls (17). Biphenyls (17) were converted to oximes (18) with hydroxylamine in the presence of sodium acetate. Oximes (18) were reduced with sodium cyanoborohydride under acidic conditions to produce to hydroxylamines (19). The hydroxylamines (19) were treated with N-chlorocarbonyl)isocyanate to produce oxadiazolidinediones (20). Thiazolidinediones were prepared from benzaldehydes (17) using known methodology [ref. J. Med. Chem., 1992, 35, 1853–1864].

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following two standard pharmacological test procedures which measure the inhibition of PTPase.

Inhibition of Tri-Phosphorylated Insulin Receptor Dodecaphosphopeptide Dephosphorylation by Rat Hepatic Protein-Tyrosine Phosphatases (PTPases)

This standard pharmacological test procedure assess the inhibition of rat hepatic microsomal PTPase activity using, as substrate, the phosphotyrosyl dodecapeptide corresponding to the 1142–1153 insulin receptor kinase domain, phosphorylated on the 1146, 1150 and 1151 tyrosine residues. The procedure used and results obtained are briefly outlined below.

Preparation of Microsomal Fraction: Rats (Male Sprague-Dawley rats (Charles River, Kingston, N.Y.) weighing 100–150 g, maintained on standard rodent chow (Purina)) are sacrificed by asphyxiation with $CO_2$ and bilateral thoracotomy. The liver is removed and washed in cold 0.85% (w/v) saline and weighed. The tissue is homogenized on ice in 10 volumes of Buffer A and the microsomes are isolated essentially as described by Meyerovitch J, Rothenberg P, Shechter Y, Bonner-Weir S, Kahn CR. Vanadate normalizes hyperglycemia in two mouse models of non-insulin-dependent diabetes mellitus. *J Clin Invest* 1991; 87:1286–1294 and Alberts B, Bray D, Lewis J, Raff M, Roberts K, Watson J D, editors. Molecular biology of the cell. New York: Garland Publishing, Inc., 1989 with minor modifications.

The liver homogenate is filtered through silk to remove any remaining tissue debris and then is centrifuged at 10,000×g for 20 minutes at 40 C. The supernatant is decanted and centrifuged at 100,000×g for 60 minutes at 40 C. The pellet, microsomes and small vesicles, is resuspended and lightly homogenized in: 20 mM TRIS-HCl (pH 7.4), 50 mM 2-mercaptoethanol, 250 mM sucrose, 2 mM EDTA, 10 mM EGTA, 2 mM AEBSF, 0.1 mM TLCK, 0.1 mM TPCK, 0.5 mM benzamidine, 25 ug/ml leupeptin, 5 ug/ml pepstatin A, 5 ug/ml;$H_5B$ antipain, 5 ug/ml chymostatin, 10 ug/ml aprotinin (Buffer A), to a final concentration of approximately 850 ug protein/ml. Protein concentration is determined by the Pierce Coomassie Plus Protein Assay using crystalline bovine serum albumin as a standard (Pierce Chemical Co., Rockford, Ill.).

Measurement of PTPase activity: The malachite green-ammonium molybdate method, as described by Lanzetta P A, Alvarez L J, Reinach P S, Candia O A was used. An improved assay for nanomolar amounts of inorganic phosphate. *Anal. Biochem.* 1979;100:95–97, and adapted for the platereader, is used for the nanomolar detection of liberated phosphate by rat hepatic microsomal PTPases. The test procedure uses, as substrate, a dodecaphosphopeptide custom synthesized by AnaSpec, Inc. (San Jose, Calif.). The peptide, TRDIYETDYYRK, corresponding to the 1142–1153 catalytic domain of the insulin receptor, is tyrosine phosphorylated on the 1146, 1150 and 1151 tyrosine residues. The microsomal fraction (83.25 ul) is preincubated for 10 min at 37 deg.C with or without test compound (6.25 ul) and 305.5 ul of the 81.83 mM HEPES reaction buffer, pH 7.4. Peptide substrate, 10.5 ul at a final concentration of 50 uM, is equilibrated to 37 deg.C in a LABLINE Multi-Blok heater equipped with a titerplate adapter. The preincubated microsomal preparation (39.5 ul) with or without drug is added to initiate the dephosphorylation reaction, which proceeds at 37 deg.C. for 30 min. The reaction is terminated by the addition of 200 ul of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 ul MG/AM/Tw to substrate and followed by 39.5 ul of the preincubated membrane with or without drug. The color is allowed to develop at room temperature for 30 min and the sample absorbances are determined at 650 nm using a platereader (Molecular Devices). Samples and blanks are prepared in quadruplicates. Screening activity of 50 uM (final) drug is accessed for inhibition of microsomal PTPases.

Calculations: PTPase activities, based on a potassium phosphate standard curve, are expressed as nmoles of phosphate released/min/mg protein. Test compound PTPase inhibition is calculated as percent of control. A four parameter non-linear logistic regression of PTPase activities using SAS release 6.08, PROC NLIN, is used for determining IC50 values of test compounds. All compounds were administered at a concentration of 50 µM. The following results were obtained using representative compounds of this invention.

| Example | % Change from Control |
|---|---|
| 4 | −28 |
| 6 | −30 |
| 7 | −74 |
| 8 | −78 |
| 9 | −20 |
| 10 | −35 |
| 12 | −68 |
| 15 | −47 |
| 16 | −20 |
| 17 | −54 |
| phenylarsine (Reference) | −57 |

Inhibition of Tri-Phosphorylated Insulin Receptor Dodecaphosphopeptide Dephosphorylation by hPTP1B This standard pharmacological test procedure assess the inhibition of recombinant rat protein tyrosine phosphatase, PTP1B, activity using, as substrate, the phosphotyrosyl dodecapeptide corresponding to the 1142–1153 insulin receptor kinase domain, phosphorylated on the 1146, 1150 and 1151 tyrosine residues. The procedure used and results obtained are briefly described below.

Human recombinant PTP1B was prepared as described by Goldstein (see Goldstein et al. *Mol. Cell. Biochem.* 109, 107, 1992). The enzyme preparation used was in microtubes containing 500–700 µg/ml protein in 33 mM Tris-HCl, 2 mM EDTA, 10% glycerol and 10 mM 2-mercaptoethanol.

Measurement of PTPase activity. The malachite green-ammonium molybdate method, as described (Lanzetta et al. *Anal. Biochem.* 100, 95, 1979) and adapted for a platereader, is used for the nanomolar detection of liberated phosphate by recombinant PTP1B. The test procedure uses, as substrate, a dodecaphosphopeptide custom synthesized by AnaSpec, Inc. (San Jose, Calif.). the peptide, TRDIYET-DYYRK, corresponding to the 1142–1153 catalytic domain of the insulin receptor, is tyrosine phosphorylated on the 1146, 1150, and 1151 tyrosine residues. The recombinant rPTP1B is diluted with buffer (pH 7.4, containing 33 mM Tris-HCl, 2 mM EDTA and 50 mM b-mercaptoethanol) to obtain an approximate activity of 1000–2000 nmoles/min/mg protein. The diluted enzyme (83.25 mL) is preincubated for 10 min at 37° C. with or without test compound (6.25 mL) and 305.5 mL of the 81.83 mM HEPES reaction buffer, pH 7.4 peptide substrate, 10.5 ml at a final concentration of 50 mM, and is equilibrated to 37° C. in a LABLINE Multi-Blok heater equipped with a titerplate adapter. The preincubated recombinant enzyme preparation (39.5 ml) with or without drug is added to initiate the dephosphorylation reaction, which proceeds at 37° C. for 30 min. The reaction is terminated by the addition of 200 mL of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 mL MG/AM/Tw to substrate and followed by 39.5 ml of the preincubated recombinant enzyme with or without drug. The color is allowed to develop at room temperature for 30 min. and the sample absorbances are determined at 650 nm using a platereader (Molecular Devices). Sample and blanks are prepared in quadruplicates.

Calculations: PTPase activities, based on a potassium phosphate standard curve, are expressed as nmoles of phosphate released/min/mg protein. Inhibition of recombinant PTP1B by test compounds is calculated as percent of phosphatase control. A four parameters non-linear logistic regression of PTPase activities using SAS release 6.08, PROC NLIN, is used for determining $IC_{50}$ values of test compounds. The following results were obtained.

| Example | IC50 (µM) |
|---|---|
| 1 | 1.66 |
| 2 | −47 (2.5 uM) |
| 3 | −56 (2.5 uM) |
| 5 | 0.85 |
| 6 | −47 (2.5 uM) |
| 7 | 1.29 |
| 8 | 1.25 |
| 9 | 0.65 |
| 10 | 0.47 |
| 11 | −40 (2.5 uM) |
| 12 | 0.13 |
| 13 | 1.15 |
| 14 | −65 (2.5 uM) |
| 15 | 0.93 |
| 16 | 1.2 |
| 17 | 0.98 |
| Phenylarsine oxide (reference standard) | 39.7 |
| Sodium orthovanadate (reference standard) | 244.8 |
| Ammonium molybdate tetrahydrate (reference standard) | 8.7 |

The blood glucose lowering activity of representative compounds of this invention were demonstrated in an in vivo standard procedure using diabetic (ob/ob) mice. The procedures used and results obtained are briefly described below.

The non-insulin dependent diabetic (NIDDM) syndrome can be typically characterizes by obesity, hyperglycemia, abnormal insulin secretion, hyperinsulinemia and insulin resistance. The genetically obese-hyperglycemic ob/ob mouse exhibits many of these metabolic abnormalities and is thought to be a useful model to search for hypoglycemic agents to treat NIDDM [Coleman, D.: Diabetologia 14: 141–148, 1978].

In each test procedure, mice [Male or female ob/ob (C57 B1/6J) and their lean litermates (ob/+ or +/+, Jackson Laboratories) ages 2 to 5 months (10 to 65 g)] of a similar age were randomized according to body weight into 4 groups of 10 mice. The mice were housed 5 per cage and are maintained on normal rodent chow with water ad libitum. Mice received test compound daily by gavage (suspended in 0.5 ml of 0.5% methyl cellulose); dissolved in the drinking water; or admixed in the diet. The dose of compounds given ranges from 2.5 to 200 mg/kg body weight/day. The dose is calculated based on the fed weekly body weight and is expressed as active moiety.

The positive control, ciglitazone (5-(4-(1-methylcyclohexylmethoxy)benzyl)-2,4-dione, see Chang, A., Wyse, B., Gilchrist, B., Peterson, T. and Diani, A. Diabetes 32: 830–838, 1983.) was given at a dose of 100 mg/kg/day, which produces a significant lowering in plasma glucose. Control mice received vehicle only.

On the morning of Day 4, 7 or 14 two drops of blood (approximetly 50 ul) were collected into sodium fluoride containing tubes either from the tail vein or after decapitation. For those studies in which the compound was administered daily by gavage the blood samples were collected two hours after compound administration. The plasma was isolated by centrifugation and the concentration of glucose is measured enzymatically on an Abbott V. P. Analyzer.

For each mouse, the percentage change in plasma glucose on Day 4, 7 or 14 is calculated relative to the mean plasma glucose of the vehicle treated mice. Analysis of variance followed by Dunett's Comparison Test (one-tailed) are used to estimate the significant difference between the plasma glucose values from the control group and the individual compound treated groups (CMS SAS Release 5.18).

The results shown in the table below shows that the compounds of this invention are antihyperglycemic agents as they lower blood glucose levels in diabetic mice.

| Example | Dose (mg/Kg) | % Change Glucose from Vehicle |
|---|---|---|
| 5 | 100 | −40[a] |
| Ciglitazone (reference standard) | 100 | −43 |

[a]Statistically ($p < 0.05$) significant.

Based on the results obtained in the standard pharmacological test procedures, representative compounds of this invention have been shown to inhibit PTPase activity and lower blood glucose levels in diabetic mice, and are therefore useful in treating metabolic disorders related to insulin resistance or hyperglycemia, typically associated with obesity or glucose intolerance. More particularly, the compounds of this invention useful in the treatment or inhibition of type II diabetes, and in modulating glucose levels in disorders such as type I diabetes. As used herein, the term modulating means maintaining glucose levels within clinically normal ranges.

Effective administration of these compounds may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

EXAMPLE 1

4-(4'-Methoxy-biphenyl-4-yl)-5-methyl-2-(4-trifluoromethyl-phenyl)-oxazole

Step a) 1-(4-bromo-2-phenyl)-propanone oxime

Sodium acetate (80.0 g, 976 mmol) was added into a mixture of 1(4-bromo-phenyl)-propanone (52.0 g, 244 mmol), hydroxylamine hydrochloride (50.8 g, 732.3 mmol), ethyl alcohol (500 mL) and water (100 mL). The reaction mixture was stirred at 60° C. for 1 hour, poured into water, and extracted with ethyl ether. The organic extracts were dried over $MgSO_4$. Evaporation and crystallization from ethyl ether/hexanes gave a white solid (49.6 g, 89% yield); MS m/e 227($M^+$); Analysis for $C_9H_{10}BrNO$: Calc'd: C, 47.39; H, 4.42; N. 6.14 Found: C, 47.42; H, 4.37; N, 5.99

Step b) 4-(4-Bromo-phenyl)-5-methyl-2-(4-trifluoromethyl-phenyl)-oxazole

Pyridine (3.55 mL, 43.86 mmol) was added into a mixture of 1-(4-bromo-phenyl)-propanone oxime (10.0 g, 43.86 mmol) and toluene (20 mL). The reaction mixture was stirred for 30 minutes, and then 4-trifluoromethyl-phenyl acetyl chloride (16.27 mL, 109.6 mmol) was added dropwise. The new mixture was stirred at 100° C. for 24 hours, and then w as poured into water and extracted with ethyl acetate. The organic extracts were dried over $MgSO_4$. Evaporation and purification by flash chromatography on silica gel (hexanes/EtAOc 40:1) gave a white solid (7.3 g, 43% yield): mp 82.84° C.; MS m/e 381 ($M^+$);
Analysis for: $C_{17}H_{11}BrF_3NO$ Calc'd: C, 53.43; H, 2.90; N, 3.67 Found: C, 53.47; H, 2.62; N, 3.43

Step c) 4-(4'-methoxy-biphenyl-4-yl)-5-methyl-2-(4-trifluoromethyl-phenyl)-oxazole 4-Methoxy-benzeneboronic acid (1.44 g, 7.19 mmol) in ethyl alcohol (5 mL) was added into a mixture of 4-(4-bromo-phenyl)-5-methyl-2-(4-trifluoromethyl-phenyl)-oxazole (2.5 g, 6.54 mmol), sodium carbonate (2N, 6.5 mL), tetrakis(triphenylphosphine)palladium(0) (0.23 g, 0.196 mmol), and toluene (200 mL). The reaction mixture was refluxed for 12 hours, cooled to room temperature, and treated with hydrogen peroxide (30%, 5 mL) for 1 hour. Then, the mixture was poured into water and extracted with ethyl acetate. The organic extracts were dried over $MgSO_4$. Evaporation and crystallization from hexanes/ethyl ether gave a white solid (2.2 g, 82% yield): mp 167–168° C.; MS m/e 409 ($M^+$);
Analysis for: $C_{24}H_{18}F_3NO_2$ Calc'd: C, 70.41; H, 4.43; N, 3.42 Found: C, 70.14; H, 4.32; N, 3.30

EXAMPLE 2

4-(4'-Methoxy-biphenyl-3-yl)-5-methyl-2-(4-trifluoromethyl-phenyl)-oxazole

The title compound was prepared from 4-(4-bromo-phenyl)-5-methyl-2-(4-trifluoromethyl-phenyl)-oxazole, and 4-methoxy-benzeneboronic acid in substantially the same manner, as described in Example 1 step c, and was obtained as a white solid, mp 93–94° C.; MS m/e 409 ($M^+$);
Analysis for: $C_{24}H_{18}F_3NO_2$ Calc'd: C, 70.41; H, 4.43; N, 3.42 Found: C, 70.25; H, 4.33; N, 3.34

EXAMPLE 3

4'-[5-Methyl-2-(4-trifluoromethyl-phenyl)-oxazol-4-yl]-biphenyl-4-ol

Boron tribromide (1.0 M, 3.91 mL, 3.91 mmol) was added dropwise into a cold (−78° C.) mixture of 4-(4'-methoxy-biphenyl-4-yl)-5-methyl-2-(4-trifluoromethyl-phenyl)-oxazole (1.6 g, 3.91 mmol), and dichloromethane (20 mL). The reaction mixture was allowed to come gradually to room temperature and stirred for 10 hours. Then, the mixture was cooled to 0° C. and methyl alcohol (5 mL) was added dropwise. After stirring for 10 minutes the mixture was poured into water and extracted with ethyl ether. The organic extracts were dried over $MgSO_4$. Evaporation and crystallization from ethyl ether/hexanes gave an off-white solid (1.4 g, 90% yield): mp 189–191; MS m/e 396 $(M+H)^+$;
Analysis for: $C_{23}H_{16}F_3NO_2$ x $0.3H_2O$ Calc'd: C, 68.92; H, 4.17; N, 3.50 Found: C, 68.97; H, 4.23; N, 3.33

EXAMPLE 4

3'-[5-Methyl-2-(4-trifluoromethyl-phenyl)-oxazol-4-yl]-biphenyl-4-ol

The title compound was prepared from 4-(4'-methoxy-biphenyl-3-yl)-5-methyl-2-(4-trifluoromethyl-phenyl)-oxazole, in substantially the same manner, as described in Example 3, and was obtained as a white solid, mp 133–135° C.; MS m/e 395 ($M^+$);
Analysis for: $C_{23}H_{16}F_3NO_2$ x $0.3H_2O$ Calc'd: C, 68.92; H, 4.17; N, 3.50 Found: C, 68.98; H, 3.83; N, 3.47

EXAMPLE 5

{4'-[5-methyl-2-(4-trifluoromethyl-phenyl)-oxazol-4-yl]-biphenyl-4-yloxy}-acetic acid Sodium hydride (0.05 g, 1.26 mmol) was added into a mixture of 4'-[5-methyl-2-(4-trifluoromethyl-phenyl)-oxazol-4-yl]-biphenyl-4-ol (0.5 g, 1.26 mmol), and N,N-dimethylformamide (5.0 mL). The reaction mixture was stirred at room temperature for 1 hour. Methyl bromoacetate (0.18 mL, 1.89 mmol) was added dropwise into the mixture. After stirring for 30 minutes, the mixture was poured into water and extracted with ethyl acetate. The organic extracts were dried over MgSO$_4$. Evaporation gave a yellow oil (0.61 g). This residue was taken in methyl alcohol (20 mL) and tetrahydrofuran (20 mL), and treated with NaOH (2.5 N, 5.0 mL) for 30 minutes. The new reaction mixture was then poured into water, acidified with HCl (2 N), and extracted with ethyl ether. The organic extracts were dried over MgSO$_4$. Evaporation and crystallization form hexanes/ethyl ether gave an off-white solid (0.42 g, 73% yield): mp 209–211; MS m/e 454 (M+H)$^+$;

Analysis for: $C_{25}H_{18}F_3NO_4$ Calc'd: C, 66.23; H, 4.00; N, 3.09 Found: C, 65.97; H, 3.93; N, 3.04

EXAMPLE 6

{3'-[5-Methyl-2-(4-trifluoromethyl-phenyl)-oxazol-4-yl]-biphenyl-4-yloxy}-acetic acid The title compound was prepared from 3'-[5-methyl-2-(4-trifluoromethyl-phenyl)-oxazol-4-yl]-biphenyl-4-ol, in substantially the same manner, as described in Example 6, and was obtained as a light yellow solid, mp 178–179° C.; MS m/e 453 (M$^+$);

Analysis for: $C_{25}H_{18}FNO_4$ x 0.3H$_2$O Calc'd: C, 65.44; H, 3.99; N, 3.05 Found: C, 65.50; H, 3.93; N, 2.92

EXAMPLE 7

2-{4'-[5-Methyl-2-(4-trifluoromethyl-phenyl)-oxazol-4-yl]-biphenyl-4-yloxy}-3-phenyl-propionic acid Diisopropyl azodicarboxylate (0.42 mL, 2.52 mmol) in benzene (10 mL) was added dropwise into a cold (0° C.) mixture of 4'-[5-methyl-2-(4-trifluoromethyl-phenyl)-oxazol-4-yl]-biphenyl-4-ol (0.5 g, 1.26 mmol), 3-phenyllactic acid methyl ester (0.45 g, 2.52 mmol), triphenylphosphine (0.66 g, 2.52 mmol), and benzene (20 mL). The reaction mixture was stirred at room temperature for 30 minutes, poured into water, and extracted with ethyl ether. The organic extracts were dried over MgSO$_4$. Evaporation gave a yellow oil (0.6 g). This residue was taken in methyl alcohol (15 mL) and tetrahydrofuran (15 mL) and treated with sodium hydroxide (2 N, 3.0 mL). The reaction mixture was stirred for 30 minutes, poured into water, acidified with HCl (2 N), and extracted with ethyl ether. The organic extracts were dried over MgSO$_4$. Evaporation and crystallization from ethyl ether/hexanes gave a white solid (0.38 g, 55% yield): mp 183–184; MS m/e 544 (M+H)$^+$;

Analysis for: $C_{32}H_{24}F_3NO_4$ Calc'd: C, 70.71; H, 4.45; N, 2.58 Found: C, 70.50; H, 4.32; N, 2.53

EXAMPLE 8

2-{3'-[5-Methyl-2-(4-trifluoromethyl-2-phenyl)-oxazol-4-yl]-biphenyl-4-yloxy}-3-phenyl-propionic acid The title compound was prepared from 3'-[5-methyl-2-(4-trifluoromethyl-phenyl)-oxazol-4-yl]-biphenyl-4-ol, in substantially the same manner, as described in Example 7, and was obtained as a white solid, mp 148–149° C.; MS m/e 543 (M$^+$);

Analysis for: $C_{32}H_{24}F_3NO_4$ Calc'd: C, 70.71; H, 4.45; N, 2.58 Found: C, 70.72; H, 4.28; N, 2.50

EXAMPLE 9

3,5-Dibromo-4'-[5-methyl-2-(4-trifluoromethyl-phenyl)-oxazol-4-yl]-biphenyl-4-ol Bromine (0.73 mL, 14.18 mmol) in acetic acid (50 mL) was added dropwise over a 30 minutes period into a cold (5° C.) mixture of 4'-(2-benzyl-benzo[b]thiophen-3-yl)-biphenyl-4-ol (2.8 g, 7.09 mmol), potassium acetate (6.95 g, 70.9 mmol), and acetic acid (200 mL). After the addition, the mixture was poured into water. The precipitated solid was filtered, washed with water and dried to afford a white solid (2.1 g; 61% yield): mp 79–81° C. MS m/e 551 (M$^+$);

Analysis for: $C_{23}H_{14}Br_2F_3NO_2$ Calc'd: C, 49.94; H, 2.55; N, 2.53 Found: C, 49.78; H, 2.46; N, 2.49

EXAMPLE 10

{3,5-Dibromo-4'-[5-methyl-2-(4-trifluoromethyl-phenyl)-oxazol-4-yl]-biphenyl-4-yloxy}-acetic acid The title compound was prepared from 3,5-dibromo-4'-[5-methyl-2-(4-trifluoromethyl-phenyl)-oxazol-4-yl]-biphenyl-4-ol, and methyl bromoacetate in substantially the same manner, as described in Example 5, and was obtained as an off-white solid, mp 165–166° C.; MS m/e 609 (M$^+$);

Analysis for: $C_{25}H_{16}Br_2F_3NO_4$ Calc'd: C, 49.13; H, 2.64; N, 2.29 Found: C, 49.24; H, 2.58; N, 2.16

EXAMPLE 11

2-{3,5-Dibromo-4'-[5-methyl-2-(4-trifluoromethyl-phenyl)-oxazol-4-yl]-biphenyl-4-yloxy}-3-phenyl-propionic acid methyl ester The title compound was prepared from 3,5-dibromo-4'-[5-methyl-2-(4-trifluoromethyl-phenyl)-oxazol-4-yl]-biphenyl-4-ol, and 3-phenyllactic acid methyl ester in substantially the same manner, as described in Example 7, and was obtained as a white solid, mp 70–72° C.; MS m/e 713 (M$^+$);

Analysis for: $C_{33}H_{24}Br_2F_3NO_4$ Calc'd: C, 55.41; H, 3.38; N, 1.96 Found: C, 55.01; H, 3.21; N, 1.99

EXAMPLE 12

2-{3,5-Dibromo-4'-[5-methyl-2-(4-trifluoromethyl-phenyl)-oxazol-4-yl]-biphenyl-4-yloxy}-3-phenyl-propionic acid The title compound was prepared from 2-{3,5-dibromo-4'-[5-methyl-2-(4-trifluoromethyl-phenyl)-oxazol-4-yl]-biphenyl-4-yloxy}-3-phenyl-propionic acid methyl ester in substantially the same manner, as described in Example 7, and was obtained as a white solid, mp 241–243° C.; MS m/e 699 (M$^+$);

Analysis for: $C_{32}H_{22}Br_2F_3NO_4$ Calc'd: C, 54.80; H, 3.16; N, 2.00 Found: C, 54.54; H, 3.03; N, 2.00

EXAMPLE 13

2-{4'-[5-methyl-2-(4-trifluoromethyl-phenyl)-oxazol-4-yl]-biphenyl-4-ylmethyl}-[1,2,4]oxadiazolidine-3,5-dione Step a) 4'-[5-Methyl-2-(4-trifluoromethyl-phenyl)-oxazol-4-yl]-biphenyl-4-carbaldehyde This compound was prepared from 4-(4-bromo-phenyl)-5-methyl-2-(4-trifluoromethyl-phenyl)-oxazole, and 4-formylbenzeneboronic acid in substantially the same manner, as described in Example 1 step c, and was obtained as an off-white solid; MS m/e 407 (M⁺);

Analysis for: $C_{24}H_{16}F_3NO_2$ Calc'd: C, 70.76; H, 3.96; N, 3.44 Found: C, 70.83; H, 3.70; N, 3.42

Step b) 4'-[5-Methyl-2-(4-trifluoromethyl-phenyl)-oxazol-4-yl]-biphenyl-4-carbaldehyde oxime This compound was prepared from 4'-[5-methyl-2-(4-trifluoromethyl-phenyl)-oxazol-4-yl]-biphenyl-4-carbaldehyde, and hydroxylamine in substantially the same manner, as described in Example 1 step a, and was obtained as an off-white solid; MS m/e 422 (M⁺);

Analysis for: $C_{24}H_{17}F_3N_2O_2$ Calc'd: C, 68.24; H, 4.06; N, 6.63 Found: C, 68.10; H, 3.82; N, 6.45

Step c) N-{4'-[5-Methyl-2-(4-trifluoromethyl-phenyl)-oxazol-4-yl]-biphenyl-4-ylmethyl}-hydroxylamine Hydrochloric acid (4 N, in dioxane, 10 mL) was added dropwise into a mixture of 4'-[5-methyl-2-(4-trifluoromethyl-phenyl)-oxazol-4-yl]-biphenyl-4-carbaldehyde oxime (1.5 g, 3.56 mmol), sodium cyanoborohydride (1.1 g, 17.81 mmol), methyl alcohol (100 mL), and tetrahydrofuran (100 mL). The reaction mixture was stirred for 1 hour poured into water, basified with sodium hydroxide (2 N), and extracted with ethyl acetate. The organic extracts were dried over MgSO₄. Evaporation and purification by flash chromatography on silica gel (EtOAc/MeOH 20:1) gave an off-white solid (1.21 g, 80% yield); MS m/e 424 (M⁺);

Analysis for: $C_{24}H_{19}F_3N_2O_2 \times H_2O$ Calc'd: C, 67.06; H, 4.60; N, 6.52 Found: C, 67.10; H, 4.34; N, 6.69

Step d) 2-{4'-[5-Methyl-2-(4-trifluoromethyl-phenyl)-oxazol-4-yl]-biphenyl-4-ylmethyl}-[1,2,4]-oxadiazolidine-3,5-dione N-(Chlorocarbonyl)isocyanate (0.2 mL, 2.6 mmol) was added dropwise into a cold (−5° C.) mixture of N-{4'-[5-methyl-2-(4-trifluoromethyl-phenyl)-oxazol-4-yl]-biphenyl-4-ylmethyl}-hydroxylamine (1.1, 2.6 mmol), and tetrahydrofuran (20.0 mL). The reaction mixture was stirred for 30 minutes, poured into water, acidified with HCl (2 N), and extracted with ethyl acetate. The organic extracts were dried over MgSO₄. Evaporation and purification by flash chromatography on acidic silica gel (hexanes/EtOAc 2:1) gave a white solid (0.68 g, 53% yield): mp 196–198; MS m/e 493 (M⁺);

Analysis for: $C_{26}H_{18}F_3N_3O_4$ Calc'd: C, 63.29; H, 3.68; N, 8.52 Found: C, 62.95; H, 3.51; N, 8.40

EXAMPLE 14

2-{4'-[5-Methyl-2-(4-trifluoromethyl-phenyl)-oxazol-4-yl]-biphenyl-3-ylmethyl}-[1,2,4]oxadiazolidine-3,5-dione This compound was prepared from 3-(4-bromo-phenyl)-5-methyl-2-(4-trifluoromethyl-phenyl)-oxazole in substantially the same manner, as described in Example 1 steps a–d, and was obtained as a white solid, mp 216–218; MS m/e 493 (M⁺);

Analysis for: $C_{26}H_{18}F_3N_3O_4$ Calc'd: C, 63.29; H, 3.68; N, 8.52 Found: C, 63.23; H, 3.43; N, 8.48

EXAMPLE 15

5-{4'-[5-Methyl-2-(4-trifluoromethyl-phenyl)-oxazol-4-yl]-biphenyl-4-yloxymethy}-1H-tetrazole Sodium hydride (0.1 g, 2.52 mmol) was added into a mixture of 4'-[5-methyl-2-(4-trifluoromethyl-phenyl)-oxazol-4-yl]-biphenyl-4-ol (1.0 g, 2.52 mmol), and N,N-dimethylformamide (5.0 mL). The reaction mixture was stirred at room temperature for 1 hour. Methyl bromoacetonitrile (0.17 mL, 2.52 mmol) was added dropwise into the mixture. After stirring for 30 minutes, the mixture was poured into water and extracted with ethyl acetate. The organic extracts were dried over MgSO₄. Evaporation gave a yellow oil (1.1 g). This residue was taken in N,N-dimethylformamide (20 mL), and treated with ammonium chloride (0.67 g, 12.6 mmol), and sodium azide (0.82 g, 12.6 mmol) at 120° C. for 10 hours. The mixture was then poured into water, acidified with HCl (2 N), and extracted with ethyl ether. The organic extracts were dried over MgSO₄. Evaporation and crystallization form hexanes/ethyl ether gave a white solid (0.49 g, 41% yield): mp 226–227; MS m/e 477 (M⁺);

Analysis for: $C_{25}H_{18}F_3N_5O_2$ Calc'd: C, 62.89; H, 3.80; N, 14.67 Found: C, 62.54; H, 3.63; N, 14.76

EXAMPLE 16

{1-Bromo-6-[5-methyl-2-(4-trifluoromethyl-phenyl)-oxazol-4-yl]-naphthalen-2-yloxy}-acetic acid Step a) 4'-(6-Methoxy-naphthalen-2-yl)-5-methyl-2-(4-trifluoromethyl-phenyl)-oxazole This compound was prepared from 1-(6-methoxy-naphthalen-2-yl)propanone oxime, and 4-trifluoromethyl-phenyl acetyl chloride in substantially the same manner, as described in Example 1 steps b, and was obtained as a white solid, mp 138–139; MS m/e 383 (M⁺);

Analysis for: $C_{22}H_{19}F_3NO_2$ Calc'd: C, 68.93; H, 4.21; N, 3.65 Found: C, 68.83; H, 4.25; N, 3.70

Step b) 6-[5-Methyl-2-(4-trifluoromethyl-phenyl)-oxazol-4-yl]-naphthalen-2-ol

This compound was prepared from 4'-(6-methoxy-naphthalen-2-yl)-5-methyl-2-(4-trifluoromethyl-phenyl)-oxazole and boron tribromide in substantially the same manner, as described in Example 3, and was obtained as a white solid, mp 188–191; MS m/e 370 (M+H)⁺;

Analysis for: $C_{21}H_{14}F_3NO_2$ Calc'd: C, 68.29; H, 3.82; N, 3.79 Found: C, 67.81; H, 3.76; N, 3.66

Step c) 1-Bromo-6-[5-ethyl-2-(4-trifluoromethyl-phenyl)-oxazol-4-yl]-naphthalen-2-ol This compound was prepared from 4'-(6-hydroxy-naphthalen-2-yl)-5-methyl-2-(4-trifluoromethyl-phenyl)-oxazole and bromine in substantially the same manner, as described in Example 9, and was obtained as an off-white solid; MS m/e 447 (M⁺);

Analysis for: $C_{21}H_{13}BrF_3NO_2$ Calc'd: C, 56.27; H, 2.92; N, 3.12 Found: C, 56.20; H, 2.66; N, 3.15

Step d) {1-Bromo-6-[5-methyl-2-(4-trifluoromethyl-phenyl)-oxazol-4-yl]-naphthalen-2-yloxy}-acetic acid This compound was prepared from 4'-(5-bromo-6-hydroxy-naphthalen-2-yl)-5-methyl-2-(4-trifluoromethyl-phenyl)-oxazole and methyl bromoacetate in substantially the same manner, as described in Example 5, and was obtained as white solid, mp 212–214° C.; MS m/e 506 (M+H)+;

Analysis for: $C_{23}H_{15}BrF_3NO_4$ Calc'd: C, 54.57; H, 2.99; N, 2.77 Found: C, 54.17; H, 2.69; N, 2.76

EXAMPLE 17

2-{1-Bromo-6-[5-methyl-2-(4-trifluoromethyl-phenyl)-oxazol-4-yl]-naphthalen-2-yloxy}-3-phenyl-propionic acid This compound was prepared from 4'-(5-bromo-6-hydroxy-naphthalen-2-yl)-5-methyl-2-(4-trifluoromethyl-phenyl)-oxazole and methyl bromoacetate in substantially the same manner, as described in Example 7, and was obtained as an off-white solid, mp 195–197° C.; MS m/e 596 (M+H)+;

Analysis for: $C_{30}H_{21}BrF_3NO_4$ Calc'd: C, 60.42; H, 3.55; N, 2.35 Found: C, 60.31; H, 3.35; N, 2.42

What is claimed is:

1. A compound of formula I having the structure

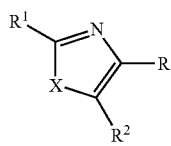

I wherein

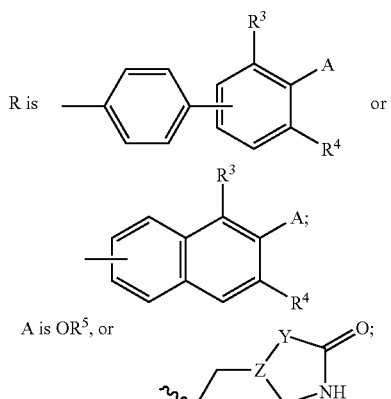

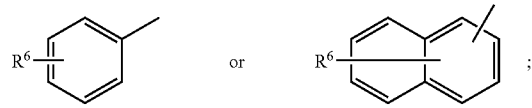

$R^1$ is alkyl of 1–6 carbon atoms, cycloalkyl of 3–8 carbon atoms, thienyl, furyl, pyridyl, $R^2$ is hydrogen, alkyl of 1–6 carbon atoms, or aryl of 6 to 10 carbon atoms;

$R^3$ and $R^4$ are independently halogen, hydrogen, alkyl of 1–12 carbon atoms, aryl of 6 to 10 carbon atoms, trifluoromethyl, alkoxyaryl of 7–14 carbon atoms, nitro, amino, carboalkoxy, carbamide, carbamate, urea, alkylsulfonamide, $-NR^7(CH_2)_mCO_2H$, arylsulfonamide, cycloalkyl of 3–8 carbon atoms, or heterocycle of 5 to 7 atom rings containing from 1 to 3 heteroatoms selected from oxygen, nitrogen, or sulfur;

$R^5$ is hydrogen, alkyl of 1–6 carbon atoms, $-CH(R^8)R^9$, $-CH_2(CH_2)_nCO_2R^{10}$, $-C(CH_3)_2CO_2R^{10}$, $-CH(R^8)(CH_2)_nCO_2R^{10}$, $-CH(R^8)C_6H_4CO_2R^{10}$, or $-CH_2$-tetrazole;

$R^6$ is hydrogen, alkyl of 1–6 carbon atoms, halogen, alkoxy of 1–6 carbon atoms, trifluoroalkyl of 1–6 carbon atoms or trifluoroalkoxy of 1–6 carbon atoms;

$R^7$ is hydrogen or alkyl of 1 to 6 carbon atoms;

$R^8$ is hydrogen, alkyl of 1–6 carbon atoms, aryl of 6–10 carbon atoms, arylalkyl of 7–15 carbon atoms, cycloalkyl of 3–8 carbon atoms, phthalic acid,

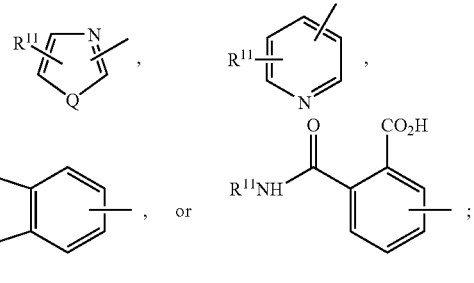

$R^9$ is $CO_2R^{12}$, $CONHR^{12}$, tetrazole, or $PO_3R^{12}$;

$R^{10}$ is hydrogen, alkyl of 1–6 carbon atoms, aryl of 6–12 carbon atoms, or aralkyl of 7–15 carbon atoms;

$R^{11}$ is alkyl of 1 to 3 carbon atoms;

$R^{12}$ is hydrogen, alkyl of 1–6 carbon atoms, aryl of 6–12 carbon atoms, or aralkyl of 7–15 carbon atoms;

X is S;
Y is O, NH, or S;
Z is C, or N;
Q is O, N, or S;
m=1–3;
n=1–6, or a pharmaceutically acceptable salt thereof.

2. The compound of claim 1, wherein R is

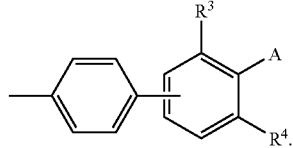

3. The compound of claim 2, wherein A is $OR^5$, wherein $R^5$ is $-CH(R^8)R^9$, $-CH_2(CH_2)_nCO_2R^{10}$, $-C(CH_3)_2CO_2R^{10}$, $-CH(R^8)(CH_2)_nCO_2R^{10}$, $-CH(R^8)C_6H_4CO_2R^{10}$, or $-CH_2$-tetrazole.

4. The compound of claim 2, wherein A is

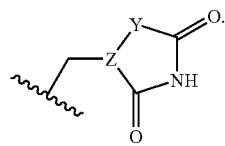

5. The compound of claim 1, wherein R is
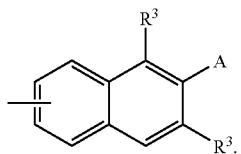
6. The compound of claim 5, wherein A is $OR^5$, wherein $R^5$ is —$CH(R^8)R^9$, —$CH_2(CH_2)_nCO_2R^{10}$, —$C(CH_3)_2CO_2R^{10}$, —$CH(R^8)(CH_2)_nCO_2R^{10}$, —$CH(R^8)C_6H_4CO_2R^{10}$, or —$CH_2$-tetrazole.
7. The compound of claim 5, wherein A is
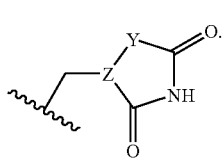
* * * * *